United States Patent [19]

Winyall et al.

[11] Patent Number: 4,631,184

[45] Date of Patent: Dec. 23, 1986

[54] DIALYTIC SILICA DENTIFRICE

[75] Inventors: Milton E. Winyall, Columbia; Cathy L. Harville, Glen Burnie, both of Md.

[73] Assignee: W. R. Grace & Co., New York, N.Y.

[21] Appl. No.: 569,687

[22] Filed: Jan. 10, 1984

[51] Int. Cl.$^4$ ................................................ A61K 7/16
[52] U.S. Cl. ...................................................... 424/49
[58] Field of Search ...................................... 424/49-58

[56] References Cited

PUBLICATIONS

Winyall, C.A. 101 #9552t (1984) of Eur. Pat. Appl. EP 107142, May 2, 1984, (U.S. appl. 434,764, Oct. 18, 1982) Particulate Dialytic Silica.
Winyall et al., C.A. 95 #45448e (1981) of Ger. Offen. 3034578, Apr. 9, 1981, (U.S. appl. 80485, Oct. 1, 1979) Silica Gel–Electrodialysis Process.
Lieb et al., C.A. 90 #44298r (1979) of U.S. 4,324,471, Nov. 7, 1978, Controlling Silica Soc Particle Size.

Primary Examiner—Shep K. Rose
Attorney, Agent, or Firm—Arthur P. Savage

[57] ABSTRACT

A dentifrice composition which contains a particulate, dialytic silica abrasive/thickening agent.

5 Claims, 1 Drawing Figure

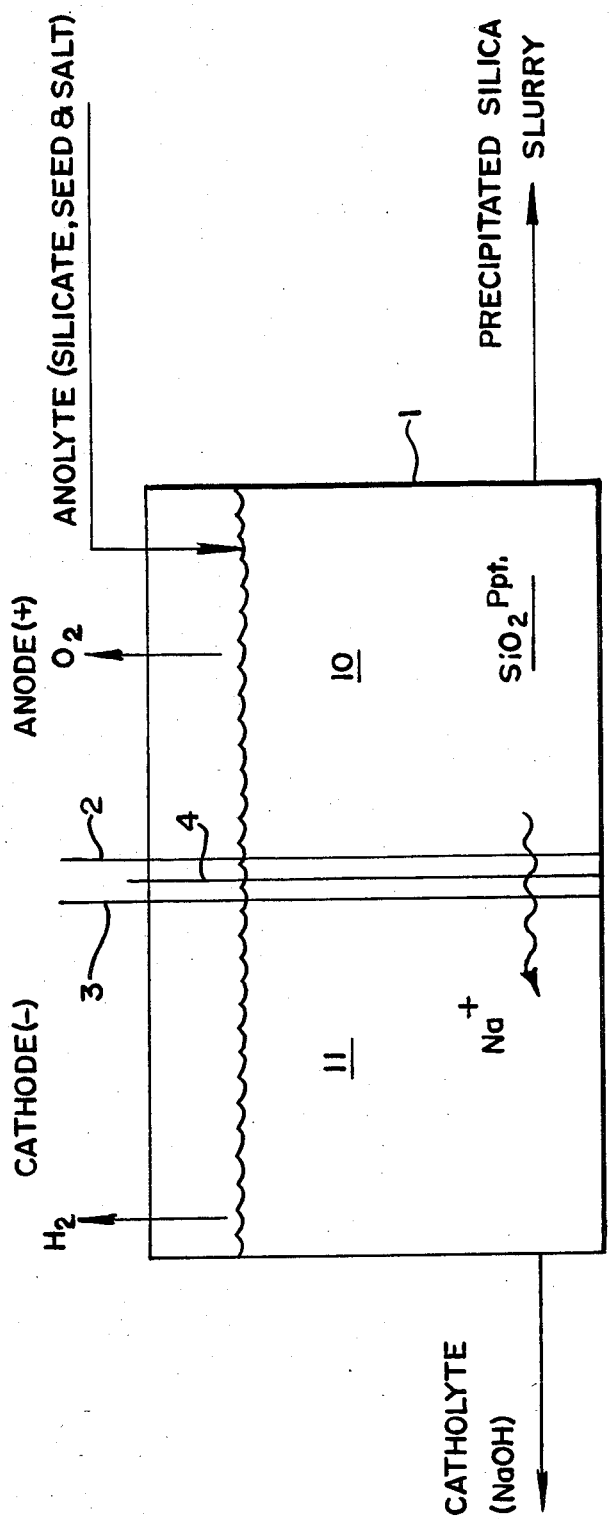

DIALYTIC SILICA DENTIFRICE

The present invention relates to dentifrice compositions, and more particularly to toothpastes which contain particulate, dialytic silica as a combination abrasive/thickening agent.

Particulate silicas have been used for many years as both abrasives and thickeners in dentifrice compositions. In some instances, toothpaste compositions will contain one type of particulate silica which serves as an abrasive and polishing agent, and a second type of silica which serves as a thickening agent.

U.S. Pat. Nos. 4,153,680 and 4,303,641 disclose the use of hydrous silica gels having a water content of from about 20 to 60 percent by weight as abrasives-polishing agents in toothpaste compositions. The use of other particulate silicas, such as silica zerogels, aerogels and pyrogenic silicas as thickening (thixotropic) agents, is also disclosed.

U.S. Pat. No. 4,336,245 discloses dentifrice compositions which include as a thickening and polishing agent a finely divided amorphous precipitated silica that contains a metal cation such as aluminum, magnesium, zinc to control the refractive index of the silica polishing/thickening component.

While particulate thickeners that have been used in toothpaste compositions and disclosed in the prior art provide an acceptable level of polishing and/or thickening capability, the industry has a significant requirement for silicas which possess a higher degree of both abrasive and thickening efficiency.

It is therefore an object of the present invention to provide improved particulate silicas which may be used as abrasives/thickening agents in toothpaste compositions.

It is a further object to provide a particulate silica polishing/thickening agent which has a high degree of both abrasive and thixotropic efficiency when used in toothpaste compositions.

It is still another object to provide a method by which the polishing and thixotropic characteristics of dentifrice compositions may be fully controlled and significantly improved in terms of effective utilization of the particulate silica component.

These and still further objects of the present invention will become readily apparent to one skilled in the art from the following detailed description, specific examples and drawing wherein the FIGURE is a cross-sectional view of an electrolysis cell that may be used to prepare the dialytic silica used in the practice of the present invention.

Broadly, our invention contemplates dentifrice compositions which include as an abrasive/thickening agent, particulate dialytic silica.

More specifically, we have found that the polishing and thixotropic properties of dentifrices may be improved by the inclusion of a particulate, dialytic silica component which is characterized by an internal pore volume of about 0.1 to 6 cc/g in a ratio of pore volume in pores greater than 3000 Å in diameter in pore volume to pore volume in pores less than 3000 Å in diameter of greater than 1.

The particulate, dialytic silica used in the practice of the present invention and the preparation thereof is disclosed in copending U.S. Ser Nos. 434,764 filed Oct. 18, 1982, abandoned, and 533,206, filed Sept. 20, 1983, now U.S. Pat. No. 508,607. As disclosed in these applications, the finely divided particulate, dialytic silica is prepared by the electrodialysis of sodium silicate solution in the presence of silica-containing nucleation particles (seeds). In general, the process used for preparing the precipitated dialytic silica comprises an eletrodialysis procedure which is conducted in an electrodialysis cell of the type shown in the FIGURE wherein an aqueous anolyte which contains a salt such as sodium sulfate or sodium nitrate and silica containing seeds having a particle size of below about 100 millimicrons is combined with an alkali metal silicate solution. The mixture is subjected to electrodialysis to remove sodium ions at a pH of from about 5 to 10.5 and to cause precipitation of the silica. The precipitated dialytic silica is then recovered from the anolyte, preferably by decantation, followed by filtration, to obtain the finely divided, i.e. 0.1 to 100 micron particulate, dialytic silica product used in the practice of the present invention. In a particularly preferred practice of the invention, the liquid phase component of the anolyte is recycled in the dialytic process, as are the alkali metal ions which are collected as an alkali metal hydroxide containing aqueous catholyte solution.

A more clear understanding of the present invention may be obtained by reference to the drawing, wherein the FIGURE is a cross-sectional view of an electrodialysis cell that may be used in the practice of the present invention. As shown in the FIGURE, the cell comprises a container 1, in which is placed an anode 2, and a cathode 3. Separating the anode and cathode is a cation permaselective membrane 4. The membrane 4 also separates anode compartment 10 from cathode compartment 11.

In operation of the cell shown in the FIGURE, an anolyte which typically comprises sodium silicate solution, colloidal silica (seeds) and sodium sulfate is added to the anode compartment 10. The initial anolyte contains about 0.01 to 2.0 percent by weight colloidal silica (dry basis), from about 0.5 to 30 percent sodium sulfate which increases the electroconductivity of the anolyte. Furthermore, the anolyte will have a pH ranging from about 2 to 12.

The cathode compartment 11 contains a catholyte solution which comprises dilute sodium hydroxide solution which contains from about 0.1 to 40 percent by weight NaOH. Subsequent to filling the anode compartment 10 and cathode compartment 11, a source of DC power (not shown) is applied to the anode and cathode. Typically, the voltage will range from about 2.5 to 10 volts and the current density will range from about 0.05 to 0.3 amps/cm$^2$. Preferably, the anolyte is constantly agitated during electrodialysis to prevent the formation of silica gel which may deposit on the anode 2.

During operation of the cell, as indicated in the FIGURE, sodium ions from the anolyte migrate through the membrane 4 to the cathode compartment 11. Sodium silicate is preferably added to the anolyte at the same rate sodium ions are removed to the catholyte to maintain a near-constant sodium ion concentration (pH) in the anolyte. Simultaneusly, oxygen is liberated at the anode 2 and hydrogen at the cathode 3. As the electrodialysis proceeds, dialytic silica precipitates in the anode compartment and may be conveniently removed as precipitated dialytic silica slurry. Furthermore, as the concentration of sodium hydroxide in the cathode compartment increases, catholyte solution is removed to maintain the desired level of sodium hydroxide in the catholyte.

The construction of the electrodialysis cell shown in the FIGURE utilizes materials which are resistant to the effects of caustic solution. Typically, the cell container is constructed of glass, plastic or stainless steel. The anode 2 comprises titanium, zirconium, niobium or hafium coated platinum group metals and are commercially available as Dimensionally Stable Anodes. The cation selective membrane 4 is preferably constructed of a polymer containing copolymerized sulfonated styrene or unsaturated carboxylic acid. Suitable commercially available membranes are described as sulfonic or carboxylic acid type membranes, such as Nafion. The cathode may be constructed of iron, steel, stainless steel or nickel. The spacing of the anode and cathode is preferably such that the space is minimized at preferably from about 1 to 5 mm. Typically, commercially available electrodialysis membranes which incorporate a built-in anode and cathode surface such as is available from General Electric may be utilized in the construction of the cells contemplated herein. While the FIGURE describes a cell which is rectangular in shape, it is contemplated that the cell and the included cathode and anode and cation selective membrane structure may be of cylindrical configuration.

The alkali metal silicate component, preferably sodium silicate, may be obtained from several commercial sources, and typically comprises an aqueous solution of water glass which has the formula 1 to 3.3 $Na_2O \cdot SiO_2$.

The finely divided silica seed component which promotes the formation of precipitated silica, has a particle size ranging typically from 1 to 30 millimicrons. The seed may be obtained from recycle anolyte or as commercially available silica sol. Furthermore, silica seeds may be prepared in the anolyte chamber (self seeding) by electrodialysis of sodium silicate under conditions which produce silica-sol, i.e. voltages of 2.5 to 10 v and current densities of 0.05 to 0.3 amps/cm$^2$. Alternatively, the seed may be prepared in the form of finely dispersed silica-alumina micells. In one preferred practice of the invention the seeds are prepared by combining sodium silicate, sodium aluminate and water in the following ratios:

| Sodium Silicate | Sodium Aluminate | Water |
|---|---|---|
| 10 | 1 | 100 to 11,000 |
| 1 | 10 | 100 to 11,000 | and subsequently reacting the mixture at a temperature of about 5 to about 100° C. for a period of 0.5 to 10 hours.

In preparing the initial seed containing anolyte a seed suspension is added to the anolyte mixture in amounts that provide from about 0.5 to 2.0 percent by weight seeds (dry basis) in the anolyte composition. The seed containing anolyte is thus held (aged) for a period of about 0.5 to 12 hours at a temperature of 20° to 80° C.

The particulate dialytic silica which is removed from the anode compartment 10 of the cell shown in the FIGURE as an aqueous slurry, typically contains from about 4 to 16 percent by weight $SiO_2$ (dry basis). The dialytic silica product has a dried particle size which will range from about 0.1 to 100 microns, and may be washed with water to remove soluble impurities such as sodium hydroxide, sodium sulfate/nitrate or the acids of these salts. The dialytic silica product may be utilized for a wide variety of purposes, including the preparation of catalysts, adsorbents, fillers and abrasives.

The dried dialytic silica typically has a particle size range of 0.1 to 100 microns and an apparent bulk density (ABD) of 0.1 to 0.6 g/cc, a surface area (SA) of 10 to 500 m$^2$/g as determined by BET, a nitrogen pore volume (N$_2$PV) of 0.1 to 2.5 cc/g in pores ranging from about 5 to about 600 Å in diameter, a total mercury pore volume (HgPV) of 1 to 6 cc/g in pores ranging from about 37 to about 10,000 Å in diameter.

The novel dialytic silica of the present invention is characterized by a unique physical structure wherein an open structure is produced. This structure contains more internal pores and a high degree of particle integrity, hardness and grindability than conventional particulate precipitated silica products. It appears that the dialytic silica particles comprise silica micelles bound together by siloxane bonds rather than hydrogen bonds present in conventional precipitated silica particles.

The dialytic silica used in the practice of the present invention possesses a unique pore volume distribution which is not found in conventional precipitated silicas. In particular, the dialytic silica contains less pore volume in pores smaller than 3000 Å in diameter and more pore volume in pores larger than 3000 Å in diameter (as determined by mercury porosimetry) than conventional precipitated silicas having a similar particle size range. The ratio of pore volume, in pores greater than 3000 Å in diameter to pore volume in pores less than 3000 Å in diameter $$\left( \text{expressed as } \frac{PV > 3000 \text{ Å}}{PV < 3000 \text{ Å}} \right)$$

for dialytic silica is greater than 1 and typically ranges from about 1.6 to about 3.5, whereas the $$\frac{PV > 3000 \text{Å}}{PV < 3000 \text{Å}}$$

for conventional precipitated silicas having similar total pore volumes typically range from about 0.4 to 1.

The dentifrice compositions of the present invention will typically contain from about 5 to 50 and preferably from 10 to 30 weight percent dialytic silica in combination with conventional dentifrice components such as surface active agents, flavoring material, buffers, humectants, preservatives coloring agents, as well as therapeutic agents such as fluoride, germicides, antibiotics and astringents. U.S. Pat. Nos. 4,153,680 and 4,303,641 describe many conventional components which may be included in the toothpaste compositions contemplated herein.

The dentifrice compositions of the present invention are evaluated using the so-called Radioactive Dentine Abrasion (RDA) powder value and toothpaste tests which are described as follows:

The radioactive dentin abrasion values (RDA) are determined in accordance with the procedure of the American Dental Association described in Hefferren, *J. Dent. Res.*, pp 563–573 (July–August 1976) with the following exceptions:

(1) Silica Powder RDA—Determined by using a slurry of 6.25 g of the silica instead of 10.0 g used in the ADA procedure. Also, the RDA's in this patent are based on a vlue of RDA=500 for calcium pyrophosphate instead of 100 assigned to that reference standard in the ADA procedure.

(2) Toothpaste RDA—Determined by using a slurry of 25 g of paste in 50 ml of $H_2O$ (based on calcium pyrophosphate RDA=100).

The procedure is outlined in U.S. Pat. No. 4,153,680.

The thixotropic controlling characteristics of the particulate, dialytic silica containing toothpaste is evaluated by use of a Brookfield Viscometer which is used as follows:

A Brookfield RVF Viscometer is equipped with a Model D Helipath unit and rotated at 4 rpm. A T-spindle (usually C.D. or E) is lowered into the jar about 5 mm into the paste. After 4 revolutions, the reading is taken and converted to centipoise (cps) value.

The Oil Adsorption test referred to herein is conducted as follows:

Mineral oil is combined with an accurately weighed 100 g portion of silica powder until a paste is formed which displays incipient wetness. Results are reported in lbs/of oil adsorbed/100 lbs of silica powder (or grams of oil adsorbed/100 g of silica powder).

Having described the basic aspects of the present invention, the following examples are given to illustrate specific embodiments thereof.

EXAMPLE 1

A series of particulate, dialytic silica samples 1A through 1G were prepared in an apparatus of the type shown in the drawing using the following general technique.

An initial anolyte comprising in some instances decantate from previous batch, sodium sulfate or nitrate to keep salt concentration at 0.15 to 0.5 molar, 40° Be' sodium silicate solution to provide 0.5 to 1.5% $SiO_2$ from sodium silicate, and DI water, as needed was heated to 60° to 90° C. The pH of the anolyte was reduced by electrolysis from about 11 to 3–6. The mixture was aged for 0 to 1 hour with the current off. 32° Be' sodium silicate solution was added to increase pH to 9 and electrolysis was continued while holding pH of anolyte at 9 by adding sodium silicate solution. Addition of sodium silicate solution was continued until the ratio of silica added after aging is 3 to 8 times amount of silica added in 40° Be' sodium silicate. Addition of sodium silicate was terminated and electrolysis continued until pH reached 3 to 7 range. The batch is allowed to settle for 12 to 24 hours. The top fraction is decanted and recycled to the next batch. The bottom fraction is reslurried with water, filtered and again washed with water and finally oven dried.

SAMPLE 1A

Initial Anolyte Composition 125 gal. decantate from previous batch;
10 lbs sodium sulfate;
15 gal DI water.

Reaction Conditions

Heat to 80°–90° C.;
Reduce pH to 9 using current/voltage of 600 A/9 V;
Age 0 minutes;
Add 346 lbs of 32° Be' sodium silicate (3.3/1 $Na_2O\cdot SiO_2$);
Reduce pH to 4.7 using current/voltage of 600 A/8.3 V;
Settle for 2.5 hours;
Decant top liquid phase;
Solids reslurried in 25 gal DI (deionized) water and filtered twice;
Dried overnight in forced draft oven at 200° C.

SAMPLE 1B

Initial Anolyte Composition 100 gal decantate from previous batch containing about 0.5 molar sodium sulfate;
30 gal deionized water;
Add 40 pounds of sodium silicate containing 5.78 pounds silicas/1.78 pounds $Na_2O$.

Reaction Conditions

Heat to 60° C.;
Reduce pH from 10.83 to 9.0 by electrodialysis at current/voltage of 1,000 A/8.3 V;
Age 0.5 hours;
Add 172 lbs of 32° Be' sodium silicate while holding pH at 9 by electrodialysis using current/voltage of 1,000 A/8.7 V;
Reduce pH to 4.6;
Settle;
Decant top liquid phase;
Reslurry solids in 25 gal deionized water and filter twice;
Dry overnight at 200° C. in forced draft oven.

SAMPLE 1C

Initial Anolyte Composition 110 gal decantate from previous batch;
30 gal deionized water;
40 pounds of sodium silicate (3.3/1 $Na_2O/SiO_2$) containing 5.78 pounds silica.

Reaction Conditions

Heat to 60° C.;
Reduce pH from 11.5 to 8.3 using current/voltage of 500 A/15 V;
Age 0.5 hours;
Add 172 pounds of 32° Be' sodium silicate while holding pH at 8.5 by electrodialysis current/voltage;
Reduce pH to 4.6 at current voltage of 500 A/5.3 V;
Settle 3.5 hours;
Decant to phase;
Twice reslurry solids in 50 gal deionized water and filter;
Dry overnight at 200° C. in forced draft oven.

SAMPLE 1D

Initial Anolyte Composition 70 gal decantate from batch 12544-7;
70 gal deionized water;
15 pounds sodium sulfate;
43.2 pounds sodium silicate containing 10 pounds of silica.

Reaction Conditions

Heat to 60° C.;
Reduce pH from 10.6 to 3.25 by electrodialysis at current/voltage of 600 A/6 V;
Age one minute;
Add 173 pounds of 32° Be' sodium silicate while holding pH at 8.5 by electrodialysis at current/voltage of 600 A/6.2 V;
Reduce pH to 4.5 by electrodialysis;
Settle 19 hours;

Decant to liquid phase;
Twice reslurry in 50 gal deionized water and filter;
Dry overnight at 200° C. in forced draft oven.

SAMPLE 1E

Initial Anolyte Composition 75 gal decantate from previous batch;
65 gal deionized water;
15 pounds sodium sulfate;
43.2 pounds of dilute sodium silicate containing 10 pounds of silica.

Reaction Conditions

Heat to 60° C.;
Reduce pH from 11.11 to 4.7 by electrodialysis using current/voltage of 600 A/5.5 V;
Age one hour;
Add 173 pounds of 32° Be' sodium silicate while holding pH between 8.0 and 10.3;
Reduce pH to 4.4 by electrodialysis;
Settle for 17 hours;
Decante top liquid phase;
Twice reslurry solids in 50 gallons deionized water and filter;
Dry overnight at 200° C. in forced draft oven.

SAMPLE 1F

Initial Anolyte Composition

About 120 gal deionized water;
34.6 pounds 40° Be' sodium silicate;
34 pounds sodium nitrate solution (about 0.4 M).

Reaction Conditions

Heat to 70° C.;
Reduce pH from 10.8 to 3 by electrodialysis at current/voltage of 500 A/7 V;
Age 0.5 hours;
Add 173 pounds of 32° Be' sodium silicate while holding anolyte at pH 8 and 70° C.;
Reduce pH to 7.2 by electrodialysis;
Settle 12 hours;
Decante top liquid phase;
Reslurry solids in 50 gal of deionized water and filter. Repeat once more;
Dry overnight at 200° C. in forced draft oven.

SAMPLE 1G

Initial Anolyte Composition 95 gal decantate from previous batch;
15 pounds sodium nitrate;
45 gal deionized water;
34.6 pounds of 40° Be' sodium silicate.

Reaction Conditions

Heat to 70° C.;
Reduce pH from 10.9 to 3 by electrodialysis at current/voltage of 500 A/5.5 V;
Age 0.5 hours;
Add 173 pounds of 32° Be' sodium silicate while holding anolyte at pH 8 and 70° C.;
Reduce pH to 7.1 by electrodialysis;
Settle 12 hours;
Twice reslurry solids in 50 gal of deionized water and filter;
Dry overnight at 200° C. in forced draft oven.

The physical, including surface area, pore volume and pore volume distribution in terms of $$\frac{PV > 3000\text{Å}}{PV < 3000\text{Å}}$$

and abrasive properties of the dialytic silicas samples 1A to 1G are summarized in Table II.

TABLE I

| Sample No. | 1A | 1B | 1C | 1D | 1E | 1F | 1G |
|---|---|---|---|---|---|---|---|
| Total Volatiles @ 1750° F. | 6.95 | 2.59 | 2.59 | 1.65 | 3.79 | 2.75 | 3.44 |
| $Na_2O$, wt. % | 0.30 | 0.69 | 1.30 | 1.01 | 0.90 | 0.53 | 1.48 |
| $SO_4$, wt. % | 0.053 | 0.62 | 0.09 | 1.18 | 1.2 | 0.49 | 0.34 |
| pH, 5% in $H_2O$ | 8.11 | 8.49 | 8.38 | 5.71 | 5.95 | 5.55 | 7.33 |
| Average Bulk Density, g/cc | .399 | .206 | .275 | .148 | .147 | .128 | .175 |
| Centrifuge Density, g/cc | .769 | .250 | .332 | .158 | .166 | .161 | .200 |
| Oil Adsorption, g/100 g $SiO_2$ | 56 | 181 | 232 | 306 | 274 | 362 | 297 |
| Average Particles Size - microns | 7.6 | 19.6 | 14.5 | 19.3 | 12.4 | 14.5 | 12.1 |
| Surface Area, $m^2$/g | 39 | 20 | 57 | 106 | 82 | 96 | 52 |
| Pore Volume, $N_2$ ml/g | .02 | .00 | .04 | .14 | .10 | .19 | .08 |
| Pore Volume, Water | .36 | .48 | .52 | 1.40 | 1.38 | 1.25 | .76 |
| Mercury Pore Volume - ml/g | | | | | | | |
| Mercury Pore Volume >3,000/+ | 0.59 | 1.75 | 2.42 | 3.21 | 3.47 | 2.84 | 2.44 |
| Mercury Pore Volume <3,000/+ | 0.34 | 0.82 | 1.07 | 1.23 | 1.01 | 1.76 | 1.26 |
| Ratio $\frac{>3000}{<3000}$ | 1.74 | 2.13 | 2.26 | 2.61 | 3.44 | 1.61 | 1.94 |
| RDA, powder value | 1639 | 1205 | 681 | 358 | 353 | — | — |

EXAMPLE 2

A series of clear-gel type toothpaste compositions were prepared by combining the following ingredients:

| | % by wt. |
|---|---|
| Sorbitol | variable } total = 84.74% |
| Dialytic Silica | variable |
| Glycerin | 5.0% |
| Sodium Lauryl Sulfate | 1.5% |
| Sodium Carboxymethyl Cellulose | 0.3% |
| Water | 0.63% |
| Sodium Saccharin | 0.20% |
| F, D & C Blue #1 (1% solution) | 0.15% |
| Na Benzoate | 0.08% |
| Polyethylene Glycol 1450 | 5.0% |
| Alcohol | 1.3% |

-continued

| | % by wt. |
|---|---|
| Flavor | 1.0% |

The toothpaste compositions were evaluated to determine viscosity and paste RDA characteristics. The evaluation data is summarized in Table II.

TABLE II

PASTE PROPERTIES OF DIALYTIC SILICA IN CLEAR GEL TOOTHPASTE

| Dialytic Silica (Sample #) | Wt. % Loading | | One Week Viscosity @ 4 rpm, cps | One Week Cohesion | Paste pH | R.I. | Paste RDA |
|---|---|---|---|---|---|---|---|
| 1C | 15% | | 71,000 | 45 | 6.48 | 1.468 | 103 |
| 1C | 20% | | 208,500 | 90 | 6.66 | 1.471 | 80 |
| 1D | 12% | | 144,000 | 80 | 6.37 | 1.4670 | 44 |
| 1D | 15% | | 625,000 | 370 | 6.50 | 1.470 | 53 |
| 1E | 12% | | 86,000 | 45 | 6.39 | 1.468 | 45 |
| 1E | 15% | | 135,000 | 75 | 6.50 | 1.466 | 44 |
| Commercial Silicas | | | | | | | |
| Control | 8.5% | Thickening Silica | | | | | |
| | 10% | Abrasive Silica | 175,000 | 95 | 6.50 | 1.463 | ≈80 |

The above data indicates that the dialytic silica can replace a dual addition of an abrasive and thickening silica in the clear-gel formulation.

EXAMPLE 3

A series of opaque toothpaste compositions were prepared by combining the following ingredients.

| | wt. % |
|---|---|
| Sorbitol | Variable ⎫ total 69.43 |
| Silica | Variable ⎭ |
| Glycerin | 18.00 |
| Water | 5.90 |
| Sodium lauryl sulfate | 1.50 |
| Trisodium phosphate | 1.50 ($Na_3PO_4 \cdot 12H_2O$) |
| Flavor oil | 1.00 |
| $TiO_2$ | 0.75 |
| Sodium phosphate | 0.70 ($NaH_2PO_4 \cdot H_2O$) |
| Xanthan gum | 0.50 |
| Carbopol 940 | 0.25 |
| Sodium fluoride | 0.22 |
| Sodium saccharin | 0.20 |
| F, D & C Blue #1 (1% solution) | 0.05 |

The properties of the toothpaste compositions are summarized in Table III.

TABLE III

OPAQUE TOOTHPASTE PROPERTIES

| | 16% Silica Formula A | 18% Silica Formula B | 20% Silica Formula C |
|---|---|---|---|
| Dialytic Silica Sample 1C | | | |
| Viscosity, cps (1 wk.) | 917,500 | 883,800 | 1,312,500 |
| pH | 6.46 | 6.48 | 6.46 |
| R.I. | 1.460 | 1.459 | 1.458 |
| Density, g/cc | 1.28 | 1.31 | 1.32 |
| RDA | 112 | 114 | 119 |
| Dialytic Silica Sample 1D | | | |
| Viscosity, cps (1 wk.) | 1,452,000 | 1,802,500 | |
| pH | 6.46 | 6.46 | |
| R.I. | 1.461 | 1.461 | |
| Density, g/cc | 1.32 | 1.35 | |
| RDA | 62 | 64 | |

| Dialytic Silica Sample 1E | |
|---|---|
| Viscosity, cps (1 wk.) | 1,370,000 |
| pH | 6.50 |
| R.I. | 1.460 |
| Density, g/cc | 1.36 |
| RDA | 61 |
| Commercial Precipitated Silica (Control) | |
| Viscosity, cps (1 wk.) | 487,500 |
| pH | 6.39 |
| R.I. | 1.458 |
| Density, g/cc | 1.32 |
| RDA | 67 |

The above results show that dialytic silica Sample No. 1C can produce higher paste viscosities and higher RDA's at lower concentrations than commercially available precipitated silica.

The above specific examples clearly indicate that use of particulate, dialytic silica in dentifrice compositions provides a means for achieving desirable abrasive and thickening properties in toothpaste. The data clearly indicates that by selecting the desired dialytic silica, a wide range of abrasive characteristics may be obtained, along with a satisfactory level of thickening.

We claim:

1. A dentifrice composition containing humectants, binders, preservatives, surfactants, flavoring agents, sweeteners or theraputic agents, and from about 5 to 50 percent by weight of a dialytic silica abrasive having an internal pore volume of about 0.1 to 6 cc/g, and a ratio of pore volume in pores greater than 3000 Å in diameter to pore volume in pores less than 3000 Å in diameter of greater than 1.

2. The dentifrice of claim 1 wherein the said ratio ranges from about 1.6 to 3.5.

3. The dentifrice of claim 1 wherein the said dialytic silica has a particle size range of from about 0.1 to 100 microns.

4. The dentifrice of claim 1 wherein the dialytic silica has a surface area of from about 10 to 500 meters$^2$/g.

5. The dentifrice of claim 1 having an RDA value of greater than about 40.

* * * * *